United States Patent [19]
Snyder

[11] Patent Number: 5,658,308
[45] Date of Patent: Aug. 19, 1997

[54] BIOACTIVE OCCLUSION COIL

[75] Inventor: Edward J. Snyder, San Jose, Calif.

[73] Assignee: Target Therapeutics, Inc., Fremont, Calif.

[21] Appl. No.: 566,799

[22] Filed: Dec. 4, 1995

[51] Int. Cl.⁶ ................................................. A61M 29/00
[52] U.S. Cl. ............................................ 606/191; 606/198
[58] Field of Search ........................... 606/191, 192, 606/194, 198; 623/1, 12; 604/30, 96, 104

[56] References Cited

U.S. PATENT DOCUMENTS

| | | | |
|---|---|---|---|
| 4,798,606 | 1/1989 | Pinchuk | 623/1 |
| 5,226,911 | 7/1993 | Chee et al. | 606/191 |
| 5,342,348 | 8/1994 | Kaplan | 606/198 |
| 5,417,708 | 5/1995 | Hall et al. | |
| 5,423,849 | 6/1995 | Engelson et al. | |
| 5,443,454 | 8/1995 | Tanabe et al. | |
| 5,462,523 | 10/1995 | Samson et al. | 604/30 |

FOREIGN PATENT DOCUMENTS

WO94/10936 5/1994 WIPO.
WO95/25480 9/1995 WIPO.

*Primary Examiner*—Michael Buiz
*Assistant Examiner*—Kevin Truong
*Attorney, Agent, or Firm*—Morrison & Foerster

[57] ABSTRACT

A thrombogenic occlusion coil for occluding a blood vessel comprising a helical metallic coil having a plurality of axially spaced windings and a plurality of strands of a thrombogenic polymer extending axially through the central core of the coil, the ends of the strands being bound together.

8 Claims, 1 Drawing Sheet

BIOACTIVE OCCLUSION COIL

TECHNICAL FIELD OF THE INVENTION

This invention relates to a medical device for forming an embolism within the vasculature of a patient. More particularly, it concerns an occlusion coil comprised of a helical wound elongated coil of a biocompatible metal and one or more strands of a bioactive material extending axially through the coil.

BACKGROUND OF THE INVENTION

Intravascular occlusion coils are used to form blockages within the vasculature for controlling internal bleeding, treating aneurysms, or reducing blood flow to tumors. These coils are typically placed at the site of the desired blockage by means of a catheter.

Several patents describe occlusive devices that include strands or fibers. U.S. Pat. No. 5,226,911 describes a helical metal coil that has one or more fiber bundles having a serpentine configuration, the loops of which extend about the individual windings of the coil. U.S. Pat. No. 5,417,708 shows a helical coil that has Dacron fibers extending radially from the coil windings. FIG. 5 of U.S. Pat. No. 5,423,849 describes a vasoocclusive device composed of a tube made of braided radiopaque fibers having a bundle of radiolucent fibers extending axially through the lumen of the braided tube. The ends of the fibers that form the bundle may be heat sealed.

DISCLOSURE OF THE INVENTION

The present invention is an occlusion coil comprising an elongated helical coil of a biocompatible metal having a plurality of helically wound, axially spaced windings and at least one strand of a bioactive (typically thrombogenic) material extending axially through the coil.

When placed in a blood vessel, blood flows through the spaces between the windings into contact with the strand(s) of thrombogenic material. That material promotes thrombosis and hastens occlusion of the vessel.

MODES FOR CARRYING OUT THE INVENTION

Figure 1:
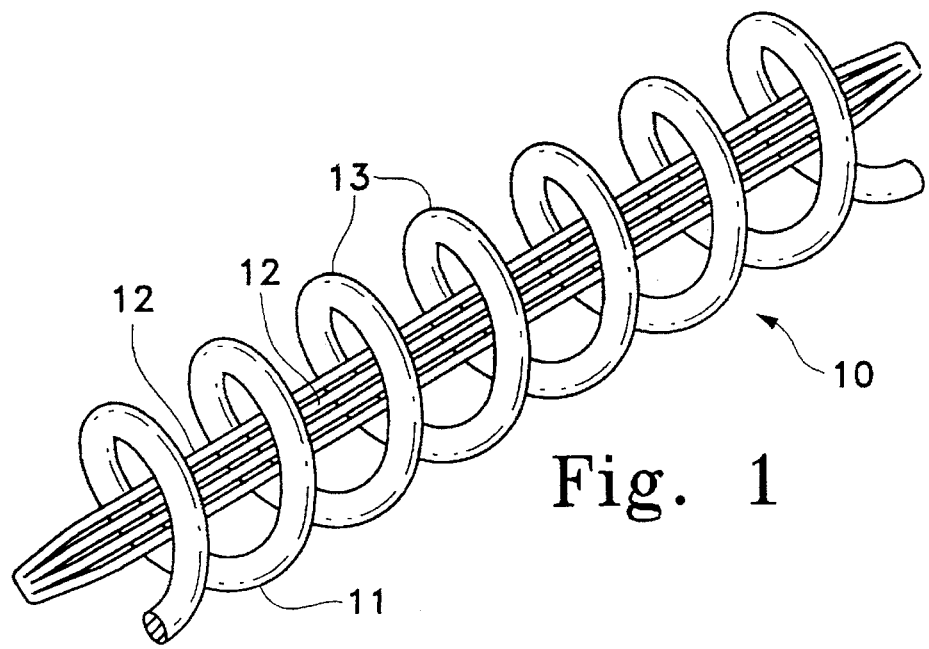
FIG. 1 is a perspective view of one embodiment of the invention.
Figure 2:
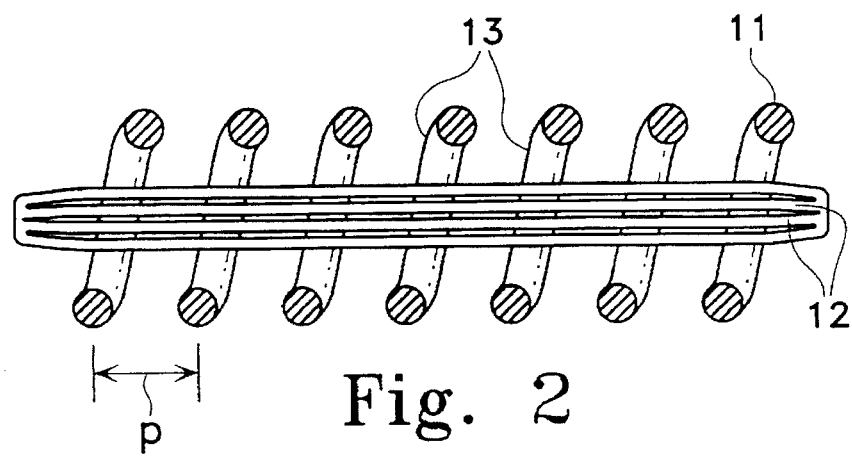
FIG. 2 is a cross-sectional view of the embodiment of FIG. 1.

FIGS. 1 and 2 show one embodiment of the inventive device. As shown in these Figures, the device, generally designated 10, is an occlusion coil. Occlusion coil 10 is composed of two principal elements: an elongated helical coil 11 and a plurality of strands or filaments 12 of a bioactive material extending axially through the open core of coil 11.

Coil 11 is a cylindrical helix made from a biocompatible metallic wire. Examples of metals that may be used to make the coil are silver, the noble metals such as gold, platinum and palladium and tungsten and alloys of such metals. The helix has a plurality of windings 13 that are axially spaced (i.e., the pitch of the windings is greater than the diameter of the wire). Although the device shown in FIGS. 1 and 2 has a circular cross-section, it could also have other cross-sectional shapes (e.g. rectangular, oval, square, triangular). The diameter of the wire will normally be 0.01 mm to 0.07 mm, preferably 0.02 mm to 0.07 mm. The diameter of the helical coil will usually be 0.2 mm to 1.0 mm, preferably 0.35 mm to 0.5 mm. The pitch, p, of the windings will usually be less than twice the diameter of the wire. The pitch may be uniform or nonuniform along the length of the coil. The length of the coil will normally be 0.2 to 100 cm, more usually 0.5 to 40.0 cm.

Strands 12 extend axially through the open central core of the helix. Although four strands are shown in the depicted embodiment, it will be appreciated that fewer or greater strands may be employed depending upon the inner diameter of the helix and the dimensions of the strands. The number/size of the strand(s) should not be such as to impede the flow of blood into the central core of the helix. Generally it is desirable to use a large number of small dimensioned strands so as to provide a large thrombogenic surface area. The ends of the strands are preferably bound together such as by thermal fusion, adhesives or mechanical means such as by tying or fastening with a fastening member. Preferably the ends are bound together in a fashion that renders them atraumatic to the vessel into which the occlusion coil is placed.

The strands are generally bioactive in some way. Included in this bioactivity are thrombogenicity and fibrogenicity. Many fibers, including those listed elsewhere herein, are thrombogenic when first placed in contact with blood and are fibrogenic after longer contact with blood fluids. The fibers used in this invention may also be used as carriers for various therapeutic materials, e.g., drugs or growth factors, either through chemical bonding or by simply soaking the device in a solution of the material.

The cross-sectional shape of the strands is not critical and may be regular (e.g. circular, rectangular, square, triangular) or irregular. The mean diameter of the strands is not critical but should be small enough to place a significant number of strands within the interior of the coil. The number of strands will usually be in the range of one to several hundred or more, but preferably 25 to 500. The strands may be linear, sinusoidal, crimped or of other axial configuration.

The strand(s) are made of one or more natural or synthetic thrombogenic polymers. Examples of thrombogenic polymers are high density polyethylene, silk, polyurethane, polyesters such as nylon or polyethylene terephthalate, polyglycolic acid, polylactic acid, etc. The strands may be made of a single homogeneous material or be formed of layers. For instance, the strand(s) may have a nonthrombogenic core coated with a thrombogenic polymer. Preferably the strands are made of polyethylene or polyethylene terephthalate.

Figure 3:
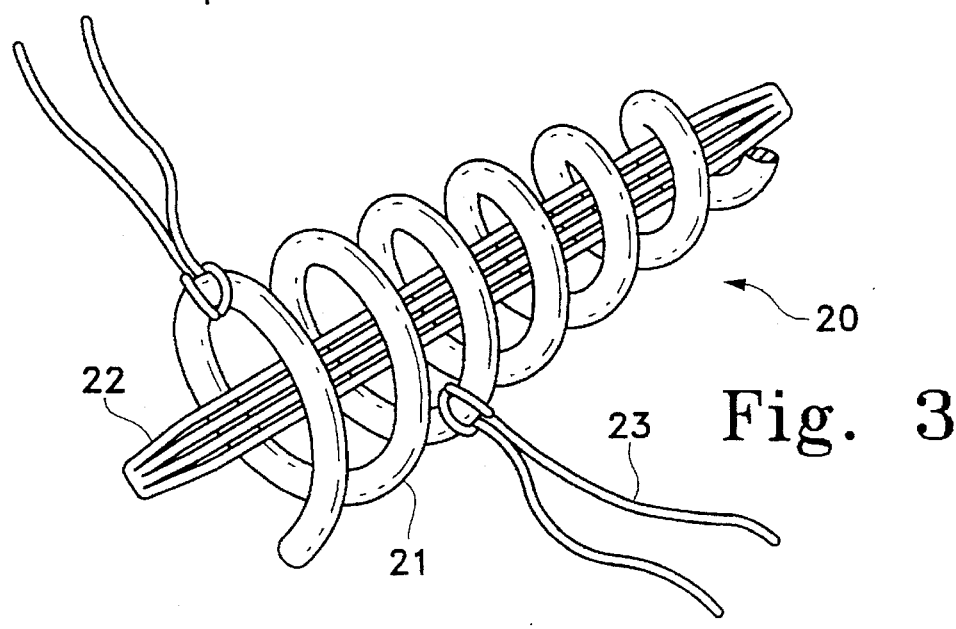
FIG. 3 is a perspective view of another embodiment of the invention.

FIG. 3 depicts another embodiment, generally designated 20, of the occlusion coil of the invention. Occlusion coil 20 is also composed of an elongated helical coil 21 and a plurality of strands 22 extending axially through coil 21. Coil 20 differs from coil 10 in that it is a conical helix rather than a cylindrical helix, and it includes a plurality of radially extending filaments 23 attached to the windings of the coil. Filaments 23 enhance the ability of the coil to occlude the site at which the coil is placed. Filaments 23 may be made of a bioactive or nonbioactive material.

The occlusion coils of the invention may be made using conventional equipment and procedures. The helical coils may be prepared by wrapping a suitable wire about a cylindrical or conical mandrel. The strand(s) are then placed axially through the core of the helix and, if a multiplicity of strands are employed, their ends bound by heat, adhesives, or mechanical means. Radial filaments may be attached to the windings of the helix by tying or with adhesives.

I claim:

1. An occlusion coil for occluding an opening within the human body comprising:
   a) an elongated helical coil of a biocompatible metal having a plurality of axial spaced windings; and
   b) a plurality of strands of a polymeric, bioactive, occlusion-causing material extending axially through the coil, each such strand having opposing ends, and wherein the ends of the strands are bound together.

2. The occlusion coil of claim 1 wherein the bioactive material is thrombogenic.

3. The occlusion coil of claim 1 wherein the bioactive material is fibrogenic.

4. The occlusion coil of claim 1 wherein the bioactive material comprises 25 to 500 strands.

5. The occlusion coil of claim 1 wherein the helical coil is a cylindrical helical coil.

6. The occlusion coil of claim 1 wherein said bioactive material is high density polyethylene, polyethylene terephthalate, or silk.

7. The occlusion coil of claim 1 further including
   (c) a plurality of radially extending fibers attached to said windings.

8. The occlusion coil of claim 1 wherein the length of the helical coil is 0.02 to 100 cm.

* * * * *